US00PP24901P3

(12) United States Plant Patent
Egger

(10) Patent No.: US PP24,901 P3
(45) Date of Patent: Sep. 16, 2014

(54) *SEDUM* PLANT NAMED 'DESERT BLONDE'

(50) Latin Name: *Sedum telephium (Syn. Hylotelephium telephium)*
Varietal Denomination: Desert Blonde

(71) Applicant: Terra Nova Nurseries, Inc., Canby, OR (US)

(72) Inventor: Janet N. Egger, Wilsonvillle, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 66 days.

(21) Appl. No.: 13/815,309

(22) Filed: Feb. 19, 2013

(65) Prior Publication Data

US 2014/0237692 P1 Aug. 21, 2014

(51) Int. Cl.
*A01H 5/00* (2006.01)

(52) U.S. Cl.
USPC ..... Plt./479

(58) Field of Classification Search
CPC ..... A01H 5/02; A01H 1/00; A01H 1/02; A01H 1/04; A01H 3/00; A01H 3/04; A01H 4/005
USPC ..... Plt./479
See application file for complete search history.

*Primary Examiner* — Annette Para
(74) *Attorney, Agent, or Firm* — Klarquist Sparkman, LLP

(57) ABSTRACT

A new and distinct hybrid of *Sedum* plant substantially as shown and described, with creamy yellow flowers in large inflorescences, blue green leaves, strong rose pink stems, rust red carpels when the seed is developing, a dense, low, mounding habit, and excellent vigor.

1 Drawing Sheet

Botanical denomination: *Sedum telephium* (Syn. *Hylotelephium telephium*).

Variety designation: 'Desert Blonde'.

BACKGROUND OF THE INVENTION

The present invention relates to a new and distinct cultivar of *Sedum telephium* and given the cultivar name of 'Desert Blonde'. *Sedum* is in the family Crassulaceae. The new cultivar is part of a planned breeding program to make short, compact, multicrown plants. The new cultivar originated from an open pollinated cross of a proprietary seedling, *Sedum* 19-1.

Compared to the seed parent, *Sedum* 19-1, the new cultivar, has a much better habit and creamy yellow flowers rather than light pink.

Compared to *Sedum* 'Yellow Xenox', U.S. Plant Pat. No. 21,528, the new variety is has creamy yellow flower buds rather than pink, a wider habit, with more crowns from young plants (an advantage to a nursery grower as the plants fill the pots quickly).

SUMMARY OF THE INVENTION

This new and unique *Sedum* is distinguished by:

1. creamy yellow flowers in large inflorescences,
2. blue green leaves,
3. strong rose pink stems,
4. rust red carpels when the seed is developing,
5. a dense, low, mounding habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the foliage of a two-year-old *Sedum* 'Desert Blonde' growing in the garden in mid-June in Canby, Oreg.

FIG. 2 shows one-year-old plants of *Sedum* 'Desert Blonde' in bloom in the trial field in late August in Canby, Oreg. The fruits are the rust red seen.

DETAILED PLANT DESCRIPTION

The following is a detailed description of the new *Sedum* hybrid based on observations of two year old specimens grown in the trial bed in full sun under typical outdoor conditions in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on *The Royal Horticultural Society Colour Chart*, $5^{th}$ edition.

Plant:

*Type*.—Herbaceous perennial.

*Hardiness*.—USDA Zone 4 to 9.

*Size*.—40 cm tall from the ground to the base of the inflorescence and 65 cm wide.

*Habit*.—Low, clumping mound.

*Vigor*.—Excellent.

Stem:

*Number*.—About 21.

*Size*.—18 cm long and 14 mm wide.

*Internode length*.—5 cm to 7 cm long.

*Color*.—Yellow Green 144A in shade and Greyed Purple 187A in sun.

*Texture*.—Succulent.

*Surface*.—Glabrous.

Leaf:

*Type*.—Simple.

*Arrangement*.—Variable.

*Shape*.—Ovate.

*Apex*.—Obtuse.

*Base*.—Sessile.

*Venation*.—Pinnate.

*Margins*.—Serrate.

*Blade size*.—Grows to 9 cm long and 5.5 cm wide.

*Surface*.—Glaucous on both sides.

*Texture*.—Thick, spongy, succulent.

*Petiole*.—Leaves sessile.

*Leaf color*.—Topside between Greyed Green 191A and N189B with the vein the same except near stem where tinted Greyed Purple 187A; bottom side Greyed Green 191A with vein 191B.

Inflorescence:

*Type*.—Terminal, corymbose, umbel-like.

*Number of flowers*.—500 to 1000 per stem (increases with age).

*Pedicels*.—2 mm to 3 mm long, 1 mm wide, glaucous, Greyed Green 191A tinted 187B in sun.

*Peduncle*.—Grows to 10 cm tall and 10 mm wide, closest to Yellow Green 147C tinted Greyed Purple 187B, glaucous.

*Size*.—Grows to 15 cm deep and 23 cm wide.

*Bloom period*.—August through September in Canby, Oreg.

Flower bud:

*Size*.—3 mm wide, 4 mm deep.

*Description*.—Ovoid.

*Color*.—Yellow Green 145D.

Flower:

*Type*.—Actinomorphic.

*Shape*.—Stellate.

*Size*.—5 mm deep and 7 mm wide.

*Corolla description*.—2 mm deep and 7 mm wide, 5 petals, each lanceolate, 5 mm long and 2.5 mm wide, margins entire, tip acuminate, glabrous on both sides, top and bottom side White NN155C.

*Calyx description*.—1.5 mm deep and 3 mm wide, stellate, 5 lobes, divided to the base, margins entire, tip acute, glabrous, Yellow Green 147C on both sides.

*Stamen description*.—10, 4.2 mm long, filaments 4 mm long and White NN155C, anthers sterile and reduced, no pollen.

*Pistil description*.—5 separate prominent carpels, each 4 mm deep and 2 mm wide, Green Yellow 1D, style 2 mm long, stigma and style Orange White 159B.

*Fragrance*.—None.

*Lastingness*.—Each stem lasts up to a month.

Fruit:

*Type*.—Ventrally dehiscent follicle, erect, attenuate.

*Fertility*.—Low.

*Size*.—4 mm wide and 5 mm deep.

*Color*.—Greyed Orange 175A.

Seed: None seen.

Disease and pest resistance or tolerance: Pest and disease resistance are typical for this type of *Sedum*. No known resistances.

I claim:

1. A new and distinct hybrid of *Sedum* plant as herein illustrated and described.

* * * * *

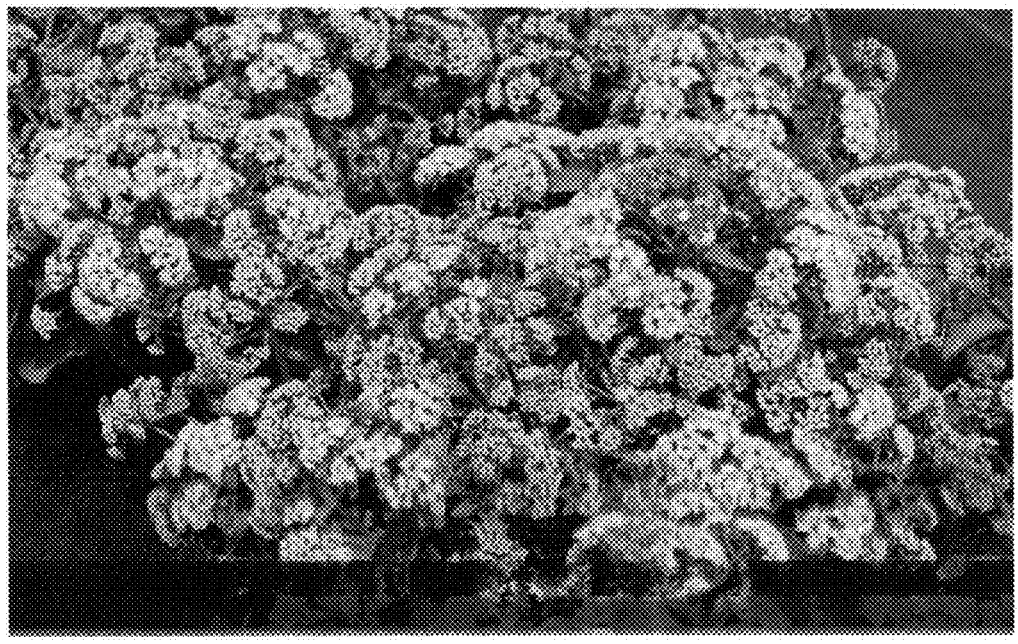

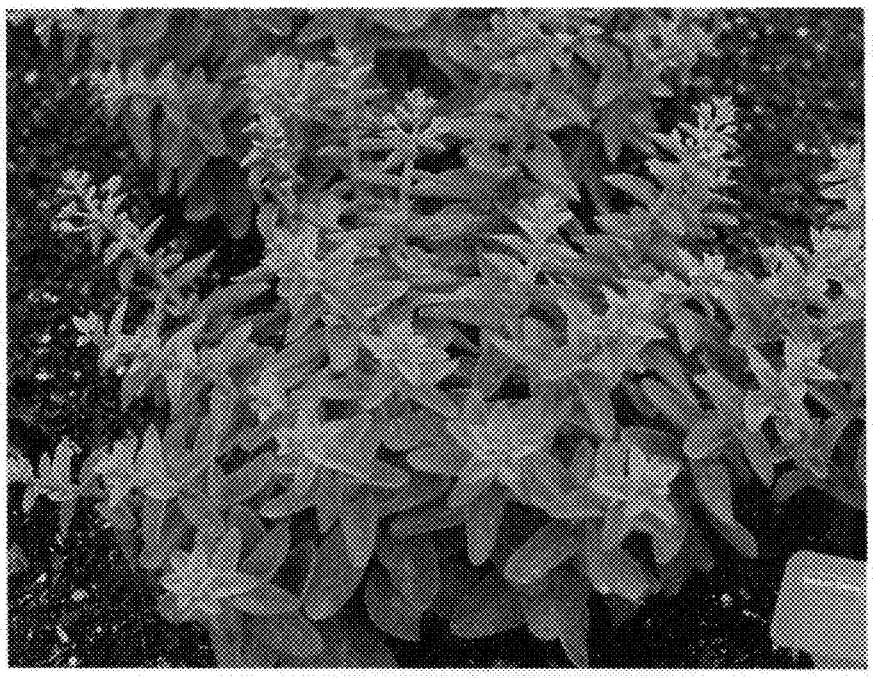
FIG. 1 above, FIG.2 below